US010403906B2

United States Patent
Itoh et al.

(10) Patent No.: US 10,403,906 B2
(45) Date of Patent: Sep. 3, 2019

(54) FUEL CELL ELECTRODE CATALYST, METHOD OF PRODUCING THE SAME, AND FUEL CELL

(71) Applicants: TOYOTA JIDOSHA KABUSHIKI KAISHA, Toyota-shi, Aichi-ken (JP); NIPPON STEEL Chemical & Material Co., Ltd., Tokyo (JP)

(72) Inventors: Yusuke Itoh, Nagoya (JP); Toru Yamamoto, Ushiku (JP)

(73) Assignees: Toyota Jidosha Kabushiki Kaisha, Toyota-shi, Aichi-ken (JP); NIPPON STEEL Chemical & Material Co., Ltd., Tokyo (JP)

( * ) Notice: Subject to any disclaimer, the term of this patent is extended or adjusted under 35 U.S.C. 154(b) by 0 days.

(21) Appl. No.: 15/832,911

(22) Filed: Dec. 6, 2017

(65) Prior Publication Data
US 2018/0166696 A1    Jun. 14, 2018

(30) Foreign Application Priority Data
Dec. 9, 2016   (JP) .................................. 2016-239594

(51) Int. Cl.
*H01M 4/00*    (2006.01)
*H01M 4/92*    (2006.01)
(Continued)

(52) U.S. Cl.
CPC ............. *H01M 4/926* (2013.01); *B01J 23/89* (2013.01); *B01J 35/10* (2013.01); *B01J 37/02* (2013.01);
(Continued)

(58) Field of Classification Search
CPC .............. H01M 4/926; H01M 4/8605; H01M 2008/1095; H01M 4/8882; B01J 37/02; B01J 23/89; B01J 37/16
See application file for complete search history.

(56) References Cited

U.S. PATENT DOCUMENTS 9,656,870 B2    5/2017  Nishi et al.
2014/0287344 A1  9/2014  Suzue et al.
(Continued)

FOREIGN PATENT DOCUMENTS

JP    2013-109856    6/2013
JP    5481748        4/2014
(Continued)

*Primary Examiner* — Cynthia H Kelly
*Assistant Examiner* — Monique M Wills
(74) *Attorney, Agent, or Firm* — Finnegan, Henderson, Farabow, Garrett & Dunner, LLP (57) ABSTRACT

A fuel cell electrode catalyst includes a carbon support having pores, and catalyst particles supported on the carbon support and containing platinum or a platinum alloy. The pores of the fuel cell electrode catalyst have a mode pore size within a range from 2 nm to 5 nm. In the pores of the fuel cell electrode catalyst, a pore volume of pores having pore sizes within the range from 2 nm to 5 nm is 0.4 $cm^3/g$ or larger. The catalyst particles have a crystallite size within the range from 2 nm to 5 nm at a platinum (220) plane. A density of the supported catalyst particles is within a range from 10% by mass to 50% by mass with respect to a total mass of the fuel cell electrode catalyst.

3 Claims, 2 Drawing Sheets

(51) Int. Cl.
- *H01M 4/88* (2006.01)
- *B01J 37/08* (2006.01)
- *B01J 37/16* (2006.01)
- *B01J 23/89* (2006.01)
- *B01J 35/10* (2006.01)
- *B01J 37/02* (2006.01)
- *C07C 11/24* (2006.01)

(52) U.S. Cl.
CPC ............... *B01J 37/08* (2013.01); *B01J 37/16* (2013.01); *H01M 4/8882* (2013.01); *C07C 11/24* (2013.01)

(56) References Cited

U.S. PATENT DOCUMENTS

| | | | |
|---|---|---|---|
| 2014/0302981 A1* | 10/2014 | Bohringer | B01D 39/06 502/10 |
| 2015/0295250 A1* | 10/2015 | Nagami | H01M 4/926 429/524 |
| 2016/0079606 A1 | 3/2016 | Mashio et al. | |
| 2016/0329571 A1* | 11/2016 | Matsumoto | B01J 31/28 |
| 2017/0194652 A1 | 7/2017 | Iijima et al. | |

FOREIGN PATENT DOCUMENTS

| | | |
|---|---|---|
| WO | WO 2014/175107 A1 | 10/2014 |
| WO | WO 2015/141810 A1 | 9/2015 |

\* cited by examiner

FUEL CELL ELECTRODE CATALYST, METHOD OF PRODUCING THE SAME, AND FUEL CELL

INCORPORATION BY REFERENCE

The disclosure of Japanese Patent Application No. 2016-239594 filed on Dec. 9, 2016 including the specification, drawings and abstract is incorporated herein by reference in its entirety.

BACKGROUND

1. Technical Field

The disclosure relates to a fuel cell electrode catalyst, a method of producing the same, and a fuel cell.

2. Description of Related Art

Fuel cells produce electricity through an electrochemical reaction between hydrogen and oxygen. Through the power generation by fuel cells, only water is produced as exhaust, in principle. Hence, fuel cells have received attention as clean power generation systems having the least adverse effect on the global environment.

In a fuel cell, fuel gas containing hydrogen is supplied to an anode (fuel electrode) side and oxidant gas containing oxygen is supplied to a cathode (air electrode) side, whereby the fuel cell develops an electromotive force. In this case, an oxidation reaction represented by Formula (1) indicated below proceeds on the anode side while a reduction reaction represented by Formula (2) indicated below proceeds on the cathode side, so that a reaction represented by Formula (3) indicated below proceeds as a whole to supply the electromotive force to an external circuit.

$$H_2 \rightarrow 2H^+ + 2e^- \quad (1)$$

$$(\tfrac{1}{2})O_2 + 2H^+ + 2e^- \rightarrow H_2O \quad (2)$$

$$H_2 + (\tfrac{1}{2})O_2 \rightarrow H_2O \quad (3)$$

Fuel cells are classified, according to the kind of an electrolyte, into polymer electrolyte fuel cells (PEFCs), phosphoric acid fuel cells (PAFCs), molten carbonate fuel cells (MCFCs), and solid oxide fuel cells (SOFCs), etc. Among these kinds of fuel cells, PEFCs and PAFCs are usually provided with an electrode catalyst including an electroconductive support, such as a carbon support, and catalytically active particles of a catalytic metal (e.g., platinum or a platinum alloy) (hereinafter, also referred to as "catalyst particles") supported on the electroconductive support.

A carbon support included in an electrode catalyst usually has a high specific surface area in order to increase a density of the supported catalyst particles. Examples of a carbon support having a high specific surface area include a carbon support having a large number of pores.

For example, Japanese Unexamined Patent Application Publication No. 2013-109856 (JP 2013-109856 A) describes a fuel cell electrode catalyst layer including catalysts, a porous support that supports the catalysts, and a polymer electrolyte. In the fuel cell electrode catalyst layer, an average particle size of the porous support is 20 nm to 100 nm, a pore volume of pores having a pore size of 4 nm to 20 nm in the porous support is 0.23 cm³/g to 0.78 cm³/g, and a mode size in a pore size distribution of the porous support is 4 nm to 20 nm. JP 2013-109856 A describes that primary pores of the porous support are formed more widely and shallowly than those in conventional porous supports. JP 2013-109856 A describes that the catalysts are supported inside the primary pores, so that the polymer electrolyte is prevented from adhering to surfaces of the catalysts in the primary pores and thus reduction in the effective reactive surface area of the catalysts can be prevented.

Japanese Patent No. 5481748 describes a dendritic carbon nanostructure including a branched carbon-containing rod-shaped or annular body, and having a BET specific surface area of 870 m²/g or larger. Japanese Patent No. 5481748 also describes a method of producing a carbon nanostructure. The method includes: a process of preparing a solution containing a metal or a salt of the metal; a process of injecting acetylene gas into the solution with ultrasonic waves applied to the solution, thereby producing a dendritic crystalline body containing the metal and carbon; a process of segregating the metal in the dendritic crystalline body by subjecting the dendritic crystalline body to a first heat treatment, thereby producing a metal-containing dendritic carbon nanostructure in which the metal is contained in a dendritic carbon nanostructure including a branched rod-shaped or annular body containing the carbon; and a process of causing the metal contained in the metal-containing dendritic carbon nanostructure to spout therefrom by subjecting the metal-containing dendritic carbon nanostructure to a second heat treatment.

WO 2015/141810 describes a support carbon material (i.e., carbon material for a support) for a polymer electrolyte fuel cell. The support carbon material is a porous carbon material in which a specific surface area $S_A$ of mesopores having a pore size of 2 nm to 50 nm determined by analyzing a nitrogen adsorption isotherm in an adsorption process by the Dollimore-Heal method is within a range from 600 m²/g to 1600 m²/g, a relative intensity ratio (IG'/IG) of a peak intensity (IG') of a peak within a G'-band range from 2650 cm⁻¹ to 2700 cm⁻¹ at a Raman spectrum with respect to a peak intensity (IG) of a peak within a G-band range from 1550 cm⁻¹ to 1650 cm⁻¹ is 0.8 to 2.2, and a peak position of the G'-band is 2660 cm⁻¹ to 2670 cm⁻¹. WO 2015/141810 also describes a method of producing the support carbon material for a polymer electrolyte fuel cell. The method includes: an acetylide production process of producing metal acetylide by injecting acetylene gas into a solution containing a metal or a salt of the metal; a first heat treatment process of heating the metal acetylide to produce a metal particle-containing intermediate containing metal particles; a second heat treatment process of subjecting the metal particle-containing intermediate to compaction molding, heating the obtained compact by increasing the temperature thereof, and causing the metal particles to spout from the metal particle-containing intermediate to obtain a carbon material intermediate; a cleaning process of cleaning the carbon material intermediate obtained in the second heat treatment process by bringing the carbon material intermediate into contact with hot concentrated nitric acid or concentrated sulfuric acid; and a third heat treatment process of heating the carbon material intermediate cleaned in the cleaning process to obtain a support carbon material.

SUMMARY

A carbon support having a large number of pores is useful for obtaining a fuel cell electrode catalyst including catalyst particles supported at a high density. However, there is still room for improvement in the performance of a fuel cell electrode catalyst including such a carbon support.

For example, in the supported catalysts for a fuel cell described in JP 2013-109856 A, the primary pores of the porous support are formed more widely and shallowly than those in conventional porous supports such that the primary pores have a cave shape. Therefore, in the supported catalysts for a fuel cell described in JP 2013-109856 A, a large number of catalyst particles are supported inside the cave-shaped primary pores. This configuration can prevent the catalyst particles in the primary pores from being covered with the polymer electrolyte. On the other hand, in the supported catalysts for a fuel cell described in JP 2013-109856 A, it is difficult for oxygen and/or hydrogen to reach the inside of the primary pores of the carbon support. As a result, there is a possibility that the gas diffusion resistance of the obtained fuel cell will be increased. In this case, there is a possibility that overvoltage will be generated at an electrode, resulting in deterioration in the performance of the fuel cell.

The disclosure provides a technique of facilitating the passage of gas inside a carbon support in a fuel cell electrode catalyst, thereby substantially preventing an increase in the gas diffusion resistance in a fuel cell.

The present inventors have found that, in the method of producing a carbon nanostructure described in Japanese Patent No. 5481748 and the method of producing a porous carbon material described in WO 2015/141810, if heat treatment conditions for a metal-containing dendritic carbon nanostructure or a metal particle-containing intermediate are optimized, it is possible to obtain a carbon support in which one or more pores having a prescribed pore size and a prescribed pore volume are formed within a prescribed range, and to cause catalyst particles to be supported at a prescribed proportion inside the one or more pores. The present inventors have also found that a fuel cell including the electrode catalyst has low gas diffusion resistance while the mass activity is maintained. The present inventors have completed the disclosure on the basis of the findings.

A first aspect of the disclosure relates to a fuel cell electrode catalyst including a carbon support having pores, and catalyst particles supported on the carbon support and containing platinum or a platinum alloy. The pores of the fuel cell electrode catalyst have a mode pore size within a range from 2 nm to 5 nm. In the pores of the fuel cell electrode catalyst, a pore volume of pores having pore sizes within the range from 2 nm to 5 nm is 0.4 $cm^3/g$ or larger. The catalyst particles have a crystallite size within the range from 2 nm to 5 nm at a platinum (220) plane. A density of the supported catalyst particles is within a range from 10% by mass to 50% by mass with respect to a total mass of the fuel cell electrode catalyst.

In the pores of the fuel cell electrode catalyst, a ratio of the pore volume of the pores having pore sizes within the range from 2 nm to 5 nm with respect to a pore volume of pores having pore sizes within a range from 2 nm to 50 nm is 0.55 or higher.

A second aspect of the disclosure relates to a fuel cell including the fuel cell electrode catalyst according to the first aspect.

A third aspect of the disclosure relates to a method of producing the fuel cell electrode catalyst according the first aspect. The method includes: a metal-containing solution preparation process of preparing a metal-containing solution containing a metal or a salt of the metal; a metal acetylide formation process of forming metal acetylide by mixing the metal-containing solution with acetylene gas; a first heat treatment process of subjecting the metal acetylide to a heat treatment at a temperature within a range from 40° C. to 80° C. to form a metal particle-containing intermediate; a second heat treatment process of subjecting the metal particle-containing intermediate to a heat treatment while a temperature is increased to a value within a range from 100° C. to 200° C. at a rate of temperature increase that is within a range from 5° C./min to 50° C./min, to cause the metal, which is contained in the metal particle-containing intermediate, to spout from the metal particle-containing intermediate to obtain a carbon support having pores; a catalytic metal salt supporting process of causing the carbon support obtained through the second heat treatment process to react with a catalytic metal material containing a salt of a catalytic metal, to cause the catalytic metal material to be supported on the carbon support; and a catalyst particle formation process of forming platinum or a platinum alloy in a metal form by reducing the salt of the catalytic metal contained in the catalytic metal material supported on the carbon support obtained through the catalytic metal salt supporting process.

The disclosure provides a technique of facilitating the passage of gas inside a carbon support in a fuel cell electrode catalyst, thereby substantially preventing an increase in the gas diffusion resistance in a fuel cell.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

1. Fuel Cell Electrode Catalyst

A fuel cell electrode catalyst according to an embodiment of the disclosure needs to include a carbon support and catalyst particles supported on the carbon support.

In general, a fuel cell electrode catalyst is provided with a carbon support having a high specific surface area for the purpose of improving the activity by causing catalyst particles to be supported on the carbon support with high dispersion and at a high density. Examples of a carbon support having a high specific surface area include a porous carbon support having a large number of pores. Such an electrode catalyst has a configuration in which catalyst particles are supported inside the pores on the carbon support. This configuration prevents the catalyst particles inside the pores from being covered with a polymer electrolyte (hereinafter, also referred to as "ionomer") when the electrode catalyst is covered with the ionomer, thereby avoiding reduction in the effective reactive surface area of the catalyst particles (see, for example, JP 2013-109856 A). On the other hand, in the electrode catalyst having such a configuration, it is difficult for oxygen gas and/or hydrogen gas to reach the inside of the pores. As a result, there is a possibility that the gas diffusion resistance of the obtained fuel cell will be increased. In this case, there is a possibility that overvoltage will be generated at an electrode, resulting in deterioration in the performance of the fuel cell.

Examples of a method of producing a porous carbon support include a method of producing a carbon nanostructure described in Japanese Patent No. 5481748 and a method of producing a porous carbon material described in WO 2015/141810. According to the methods described in Japanese Patent No. 5481748 and WO 2015/141810, a porous carbon material can be obtained by causing a metal, which has been introduced in advance into an intermediate, to spout from the intermediate through a heat treatment.

In a fuel cell electrode catalyst, an average particle size of catalyst particles is usually approximately 3 nm, and an average thickness of an ionomer with which the electrode catalyst is covered is usually approximately 5 nm. Hence, in order to obtain a fuel cell electrode catalyst in which catalyst particles are supported at a high density inside pores on a carbon support and the catalyst particles inside the pores can be substantially prevented from being covered with an ionomer, a mode size of the pores in the porous carbon support is preferably within a range from approximately 3 nm to approximately 5 nm. However, according to the methods in the conventional techniques, it has been difficult to accurately adjust the size of the pores in the porous carbon support to values within a desired range.

The present inventors have found that, in the method of producing a carbon nanostructure described in Japanese Patent No. 5481748 and the method of producing a porous carbon material described in WO 2015/141810, if heat treatment conditions for a metal-containing dendritic carbon nanostructure or a metal particle-containing intermediate are optimized, it is possible to obtain a carbon support in which one or more pores having a prescribed pore size and a prescribed pore volume are formed within a prescribed range, and to cause catalyst particles to be supported at a prescribed proportion inside the one or more pores. The present inventors have also found that a fuel cell including the electrode catalyst has low gas diffusion resistance while the mass activity is maintained. Employment of the fuel cell electrode catalyst having the foregoing features according to the embodiment of the disclosure can substantially prevent deterioration in the fuel cell performance, such as the mass activity.

The gas diffusion resistance and the mass activity of the fuel cell electrode catalyst according to the embodiment of the disclosure can be evaluated, for example, by producing a membrane electrode assembly (MEA) of a fuel cell including the fuel cell electrode catalyst as an anode and/or a cathode, and subjecting the MEA to gas diffusion resistance and mass activity evaluation tests that are usually adopted in this technical field.

Figure 1:
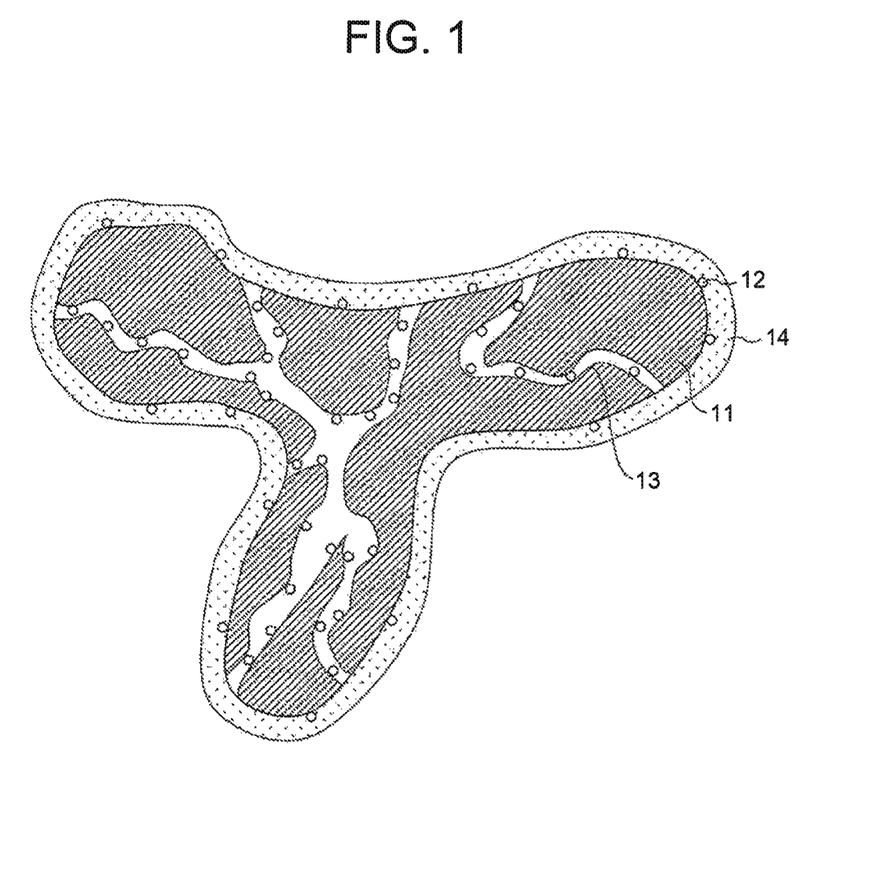
FIG. 1 is a sectional view illustrating the shape a fuel cell electrode catalyst according to an embodiment of the disclosure.

FIG. 1 is a sectional view illustrating the shape the fuel cell electrode catalyst according to the embodiment of the disclosure. The fuel cell electrode catalyst according to the present embodiment includes a carbon support 11 and catalyst particles 12 supported on the carbon support 11. The carbon support 11 included in the fuel cell electrode catalyst according to the present embodiment has pores 13. The number of pores 13 is usually two or more. At least one end portion of each pore 13 may form an opening on a surface of the carbon support 11, and the remaining end portion of the pore 13 may be positioned inside the carbon support 11. Alternatively, all end portions of each pore 13 form openings on the surface of the carbon support 11. The pores 13 of the fuel cell electrode catalyst according to the present embodiment need to have a mode pore size within a range from 2 nm to 5 nm. In the disclosure, the mode size of the pores in the fuel cell electrode catalyst means a pore size that appears most frequently in a pore size distribution of the fuel cell electrode catalyst. The pores of the fuel cell electrode catalyst according to the present embodiment usually mean the pores 13 in the carbon support 11. The mode pore size is preferably within a range from 3 nm to 4.5 nm. As described later, the catalyst particles included in the fuel cell electrode catalyst according to the present embodiment have a crystallite size within the range from 2 nm to 5 nm at a platinum (220) plane. In the fuel cell electrode catalyst according to the present embodiment, the catalyst particles are more likely to be supported inside the pores, when the mode pore size of the electrode catalyst is equal to or larger than the lower limit. As illustrated in FIG. 1, an ionomer 14 is less likely to enter the pores 13 when the mode size of the pores 13 of the electrode catalyst is equal to or smaller than the upper limit. When such a fuel cell electrode catalyst is applied to a fuel cell, it is possible to prevent the catalyst particles from being directly covered with the ionomer, thereby substantially preventing reduction in the effective reactive surface area of the catalyst particles. Hence, deterioration in the fuel cell performance can be substantially prevented when the mode pore size of the fuel cell electrode catalyst according to the present embodiment is within the above-described range. In the disclosure, the surface of the carbon support does not include surfaces of the pores.

The mode pore size of the fuel cell electrode catalyst according to the present embodiment can be determined, for example, on the basis of a pore size exhibiting the maximum value of a logarithmic derivative pore volume in a pore size distribution curve that is obtained by, for example, the Barrett-Joyner-Halenda (BJH) method, and that indicates the relationship between the pore size of the electrode catalyst and the logarithmic derivative pore volume. The pore size distribution curve can be obtained, for example, by the following procedures. In nitrogen gas of 77.4 K (boiling point of nitrogen), an amount (ml/g) of the nitrogen gas adsorbed on the carbon support is measured at each pressure P (mmHg) of the nitrogen gas while the pressure P is gradually increased. Subsequently, a value obtained by dividing the pressure P (mmHg) by a saturated vapor pressure $P_0$ (mmHg) of the nitrogen gas is defined as a relative pressure $P/P_0$. The nitrogen gas adsorbed amount corresponding to each relative pressure $P/P_0$ is plotted to obtain an adsorption isotherm. Then, the pore size distribution of the carbon support is determined according to the BJH method from the adsorption isotherm. In this way, the pore size distribution curve can be obtained. As for the BJH method, see, a literature known in the art, for example, J. Am. Chem. Soc., 1951, Vol. 73, pp. 373 to 380.

In the pores of the fuel cell electrode catalyst according to the present embodiment, a pore volume of pores having pore sizes within the range from 2 nm to 5 nm needs to be 0.4 $cm^3/g$ or larger. In the disclosure, the pore volume of pores having specific pore sizes among the pores of the fuel cell electrode catalyst means the sum of pore volumes of the pores having the specific pore sizes among the pores. The pore volume of pores having pore sizes within the range from 2 nm to 5 nm is preferably 0.5 cm$^3$/g or larger. In the pores of the fuel cell electrode catalyst according to the present embodiment, pores can communicate with each other inside the carbon support, when the pore volume of pores having pore sizes within the range from 2 nm to 5 nm is equal to or larger than the lower limit. This configuration facilitates diffusion of oxygen gas and/or hydrogen gas through the pores that communicate with each other, thereby reducing gas diffusion resistance. Further, water generated by a reaction is easily discharged to the outside of the carbon support through the pores that communicate with each other.

In the pores of the fuel cell electrode catalyst according to the present embodiment, the ratio of the pore volume of pores having pore sizes within the range from 2 nm to 5 nm with respect to a pore volume of pores having pore sizes within a range from 2 nm to 50 nm is preferably 0.55 or higher, and is more preferably 0.6 or higher. In the pores of the fuel cell electrode catalyst according to the present embodiment, the proportion of the pores having pore sizes within the range from 2 nm to 5 nm to all the pores is large when the ratio is equal to or higher than the lower limit. In this case, the catalyst particles are more likely to be supported inside the pores. Further, in this case, the ionomer is less likely to enter the pores. When such a fuel cell electrode catalyst is applied to a fuel cell, it is possible to prevent the catalyst particles from being directly covered with the ionomer, thereby substantially preventing reduction in the effective reactive surface area of the catalyst particles.

The pore volume of pores having pore sizes within the range from 2 nm to 5 nm or that within the range from 2 nm to 50 nm in the pores of the fuel cell electrode catalyst according to the present embodiment can be determined, for example, on the basis of a pore size distribution curve that indicates the relationship between pore size of the electrode catalyst and the cumulative pore volume.

The carbon support having the foregoing configuration can be obtained by a method of producing a fuel cell electrode catalyst of the embodiment of the disclosure as described below.

The catalyst particles included in the fuel cell electrode catalyst according to the present embodiment need to contain platinum (Pt) or a platinum alloy as a catalytic metal. The catalyst particles preferably contain a platinum alloy. The platinum alloy usually contains Pt and one or more kinds of other metals. In this case, examples of one or more kinds of other metals contained in a platinum alloy include cobalt (Co), gold (Au), palladium (Pd), nickel (Ni), manganese (Mn), iridium (Ir), iron (Fe), copper (Cu), titanium (Ti), tantalum (Ta), niobium (Nb), yttrium (Y), and lanthanoid elements, such as gadolinium (Gd), lanthanum (La), and cerium (Ce). When the catalyst particles included in the fuel cell electrode catalyst according to the present embodiment contain the catalytic metal described above, the electrode catalyst having high activity and high durability can be obtained.

The composition of the catalyst particles included in the fuel cell electrode catalyst according to the present embodiment and the density of the supported catalyst particles can be determined, for example, by dissolving the catalytic metal contained in the catalyst particles from the electrode catalyst into aqua regia, and then quantifying catalytic metal ions in the solution with the use of an inductively coupled plasma (ICP) atomic emission spectrometer.

The catalyst particles included in the fuel cell electrode catalyst according to the present embodiment need to have a crystallite size within the range from 2 nm to 5 nm, preferably within a range from 2 nm to 3.5 nm, at a Pt (220) plane.

In general, the particle size of the catalyst particles included in the fuel cell electrode catalyst is increased with an increase in the burning temperature after the catalyst particles are supported on the carbon support in the production of the fuel cell electrode catalyst. Specific conditions for obtaining the catalyst particles having a crystallite size within the above-described range at a Pt (220) plane can be determined based on the correlation with the conditions for a burning treatment, which are acquired through a preliminary experiment carried out in advance, in consideration of the foregoing factors. According to this method, it is possible to obtain the catalyst particles having a crystallite size within the above-described range at a Pt (220) plane.

The crystallite size at a Pt (220) plane of the catalyst particles can be determined, for example, in the following method. The X-ray diffraction (XRD) of the catalyst particles included in the fuel cell electrode catalyst according to the present embodiment is measured with the use of an XRD apparatus. A normal distribution curve is fitted to a peak pattern corresponding to the (220) plane of the catalytic metal crystals contained in the catalyst particles, in the obtained XRD. A half width of the fitted normal distribution curve is calculated. The crystallite size at a Pt (220) plane of the catalyst particles is calculated in a method known in the art (JISH7805, etc.) on the basis of the obtained half width.

The catalyst particles included in the fuel cell electrode catalyst according to the present embodiment-need to be supported at a density of 10% to 50% by mass. In the disclosure, the density of the supported catalyst particles means a percentage of the mass of the catalyst particles with respect to the total mass of the electrode catalyst. The density of the supported catalyst particles is preferably within a range from 20% by mass to 40% by mass.

The fuel cell electrode catalyst according to the present embodiment may be applied to each of an anode and a cathode of a fuel cell. Hence, another embodiment of the disclosure relates to a fuel cell including the fuel cell electrode catalyst according to the foregoing embodiment. The fuel cell according to the present embodiment includes an anode and a cathode. At least one of the anode and the cathode includes the fuel cell electrode catalyst according to the foregoing embodiment and an ionomer. The anode, the cathode, and the ionomer included in the fuel cell according to the present embodiment may be selected as appropriate from materials usually used in this technical field. When the fuel cell electrode catalyst according to the foregoing embodiment is applied to at least one of the anode and the cathode, it is possible to avoid an increase in the gas diffusion resistance, thereby substantially preventing deterioration in the fuel cell performance. Hence, when the fuel cell according to the present embodiment is applied to, for example, automobiles, it is possible to substantially prevent deterioration in the performance even in long-term use, thereby stably delivering high performance.

2: Method of Producing Fuel Cell Electrode Catalyst

The present inventors have found that, in the method of producing a carbon nanostructure described in Japanese Patent No. 5481748 and the method of producing a porous carbon material described in WO 2015/141810, if heat treatment conditions for a metal-containing dendritic carbon nanostructure or a metal particle-containing intermediate are optimized, it is possible to obtain a carbon support in which pores having a prescribed pore size and a prescribed pore volume are formed within a prescribed range, and to obtain a fuel cell electrode catalyst in which catalyst particles at a prescribed proportion are supported inside the pores. Hence, another embodiment of the disclosure relates to a method of producing the fuel cell electrode catalyst according to the foregoing embodiment. The method according to the present embodiment needs to include a metal-containing solution preparation process, a metal acetylide formation process, a first heat treatment process, a second heat treatment process, a catalytic metal salt supporting process, and a catalyst particle formation process. Each of these processes will be described below.

2-1: Metal-Containing Solution Preparation Process

The method according to the present embodiment includes the metal-containing solution preparation process of preparing a metal-containing solution containing a metal or a salt of the metal. In this process, the metal contained in the metal-containing solution is preferably silver. The salt of the metal is preferably silver nitrate. This process may be carried out, for example, in the same way as in a process in the method described in Japanese Patent No. 5481748 or WO 20157141810.

2-2: Metal Acetylide Formation Process

The method according to the present embodiment includes the metal acetylide formation process of forming metal acetylide by mixing the metal-containing solution with acetylene gas. This process may be carried out, for example, in the same way as in a process in the method described in Japanese Patent No. 5481748 or WO 2015/141810. Metal acetylide having a dendritic configuration is formed by carrying out this process.

2-3: First Heat Treatment Process

The method according to the present embodiment includes the first heat treatment process of subjecting the metal acetylide to a heat treatment, thereby forming a metal particle-containing intermediate. This process may be carried out, for example, in the same way as in a process in the method described in Japanese Patent No. 5481748 or WO 2015/141810.

In this process, the temperature at which the metal acetylide is subjected to the heat treatment is preferably within a range from 40° C. to 80° C., and is more preferably within a range from 60° C. to 80° C. The time over which the metal acetylide is subjected to the heat treatment is preferably 12 hours or longer. When this process is carried out under the above-described conditions, it is possible to form a metal-containing dendritic carbon nanostructure containing the metal and having a dendritic configuration.

2-4: Second Heat Treatment Process

The method according to the present embodiment includes the second heat treatment process of subjecting the metal particle-containing intermediate to a heat treatment while increasing the temperature, thereby causing the metal contained in the metal particle-containing intermediate to spout therefrom. This process may be carried out, for example, in the same way as in a process in the method described in Japanese Patent No. 5481748 or WO 2015/141810.

In this process, the rate of temperature increase during the heat treatment of the metal particle-containing intermediate is preferably within a range from 5° C./min to 50° C./min, and is more preferably within a range from 10° C./min to 40° C./min. The temperature at which the metal particle-containing intermediate is subjected to the heat treatment after the temperature of the metal particle-containing intermediate is increased is preferably within a range from 100° C. to 200° C., and is more preferably within a range from 160° C. to 170° C. The time over which the metal particle-containing intermediate is subjected to the heat treatment is preferably within a range from 1 minute to 60 minutes, and is more preferably within a range from 10 minutes to 30 minutes. When this process is carried out under the above-described conditions, it is possible to cause the metal particles to spout from the metal particle-containing intermediate, thereby forming pores having a prescribed shape in a carbon support. As a result, the carbon support having pores is obtained. The pores of the carbon support obtained through this process usually have a mode pore size within the range from 2 nm to 5 nm, and a pore volume of pores having pore sizes within the range from 2 nm to 5 nm is 0.4 $cm^3/g$ or larger. When the carbon support having pores obtained through this process is subjected to the catalytic metal salt supporting process and the catalyst particle formation process described below, it is possible to form a fuel cell electrode catalyst in which a mode pore size is within the range from 2 nm to 5 nm and a pore volume of pores having pore sizes within the range from 2 nm to 5 nm is 0.4 $cm^3/g$ or larger.

In this process, a cleaning process and a third heat treatment process may be carried out, if desired. In the cleaning process, the intermediate obtained by causing the metal particles to spout from the metal particle-containing intermediate is cleaned by bringing the intermediate into contact with hot concentrated nitric acid or concentrated sulfuric acid. In the third heat treatment process, the intermediate cleaned through the cleaning process is heated to obtain a carbon support having one or more pores. The cleaning process and the third heat treatment process may be carried out, for example, in the same way as in processes in the method described in Japanese Patent No. 5481748 or WO 2015/141810.

2-5: Catalytic Metal Salt Supporting Process

The method according to the present embodiment includes the catalytic metal salt supporting process of causing the carbon support obtained through the second heat treatment process to react with a catalytic metal material containing a salt of a catalytic metal, so that the catalytic metal material is supported on the carbon support.

When the catalytic metal is, for example, Pt, the salt of the catalytic metal contained in the catalytic metal material that is used in this process is preferably hexahydroxoplatinum nitrate, dinitrodiamine platinum(II) nitrate, or a hexahydroxoplatinum-amine complex. When the catalytic metal is a platinum alloy, the catalytic metal material used in this process preferably contains a salt of another metal to be contained in the platinum alloy. In this case, the salt of the other metal to be contained in the platinum alloy is preferably a salt of the other metal and nitric acid or acetic acid, and is more preferably cobalt nitrate, nickel nitrate, manganese nitrate, cobalt acetate, nickel acetate, or manganese acetate.

This process may be carried out by a reaction usually used in this technical field, according to, for example, a colloid method or a deposition-precipitation method.

2-6: Catalyst Particle Formation Process

The method according to the present embodiment includes the catalyst particle formation process of forming platinum or a platinum alloy in a metal form by reducing the salt of the catalytic metal contained in the catalytic metal material supported on the carbon support obtained through the catalytic metal salt supporting process.

In this process, the salt of the catalytic metal contained in the catalytic metal material supported on the carbon support is reduced by subjecting the carbon support that supports the catalytic metal material to a heat treatment. Thus, catalyst particles containing platinum or a platinum alloy in a metal form and supported on the carbon support are formed. The temperature in the heat treatment is preferably within a range from 40° C. to 90° C. The heat treatment is preferably carried out under the presence of a reductant, such as ethanol, hydrazine, methanol, propanol, sodium borohydride, or isopropyl alcohol. When the carbon support that supports the catalytic metal material is subjected to the heat treatment under the above-described conditions, it is possible to reduce the salt of the catalytic metal, thereby forming catalyst particles containing platinum or a platinum alloy as the catalytic metal.

This process may further include, if desired, a burning process of burning the electrode catalyst including the catalyst particles formed through the heat treatment. In the burning process, the temperature at which the electrode catalyst including the catalyst particles is burned is preferably within a range from 80° C. to 900° C. When the burning process is carried out, it is possible to adjust the particle sizes of the catalyst particles to values within the above-described range. When the catalytic metal material contains a salt of another metal to be contained in a platinum alloy, Pt and the other metal can be alloyed from the salt of the other metal to form the platinum alloy in a metal form.

With the method of producing a fuel cell electrode catalyst according to the present embodiment, it is possible to produce a fuel cell electrode catalyst having the configuration as described above.

Hereinafter, the disclosure will be described in more detail with reference to Examples. However, Examples do not limit the technical scope of the disclosure.

1: Preparation of Electrode Catalyst
I-1: Preparation of Carbon Support

Carbon support used in Examples and Comparative Examples were prepared according to the method described in Japanese Patent No. 5481748 or WO 2015/141810. The heat treatment temperature in the first heat treatment process, and the rate of temperature increase and the heat treatment temperature in the second heat treatment process are illustrated in Table 1.

TABLE 1

| | First heat treatment process Heat treatment temperature (° C.) | Second heat treatment process | |
|---|---|---|---|
| | | Rate of temperature increase (° C./min) | Heat treatment temperature (° C.) |
| Example 1 | 60 | 10 | 160 |
| Example 2 | 60 | 20 | 160 |
| Comparative Example 1 | 60 | 90 | 160 |
| Comparative Example 2 | 60 | 60 | 160 |

I-2: Supporting of Catalyst Particles

Then, 10 g of the carbon support obtained by the procedures of I-1 was dispersed in pure water. By adding an aqueous nitric acid solution to the dispersion, the pH of the dispersion was adjusted to 2 or lower. A dinitrodiamine platinum(II) nitrate solution containing Pt in a charge amount (4.29 g), with which the amount of supported Pt is 30% by mass with respect to the total mass of a final product, and 50 g of 99.5% ethanol were added in this order to the dispersion. The mixture was thoroughly stirred so as to be in a substantially homogeneous state, followed by heating under conditions of 60° C. to 90° C. and 3 hours. After the completion of heating, the obtained dispersion was repetitively filtered and washed until the electroconductivity of the filtrate became 5 S/cm or lower. The obtained solid matter was dried by air blowing at 80° C. for 15 hours. The powder thus dried was subjected to a heat treatment at 700° C. in argon gas. The obtained carbon support that supports 30% by mass of Pt was dispersed in pure water having a mass of 30 times the total mass of the carbon support. An aqueous cobalt nitrate solution was delivered by drops into the dispersion until the molar ratio of Pt to Co became 7. The aqueous cobalt nitrate solution was prepared by dissolving commercially available cobalt nitrate hexahydrate into pure water. After the delivery of the aqueous cobalt nitrate solution by drops, sodium borohydride diluted with pure water was delivered by drops into the obtained mixture until the molar ratio of Pt to Co became a value within a range from 1 to 6. After the delivery of the sodium borohydride by drops, the obtained mixture was stirred for 1 to 20 hours. After the stirring, the obtained dispersion was repetitively filtered and washed until the electroconductivity of the filtered drainage became 5 µS/cm or lower. The obtained powder cake was dried by air blowing at 80° C. for IS hours. The powder thus dried was subjected to a heat treatment for alloying at 800° C. in argon gas. The powder of electrode catalyst was obtained by the foregoing procedures.

II: Evaluation of Electrode Catalyst
II-1: Density of Supported Catalytic Metal

Pt and Co that are the catalytic metals were dissolved from a prescribed amount of the electrode catalyst in each of Examples and Comparative Examples into aqua regia. Catalytic metal ions in the obtained solution were quantified by an ICP atomic emission spectrometer (ICPV-8100; manufactured by Shimadzu Corporation). The densities of the supported catalytic metals in the electrode catalyst (% by mass with respect to the total mass of the electrode catalyst) were determined from the volume of the solution, the quantitative values of the catalytic metals in the solution, the charge amounts of the catalytic metals, and the charge amount of carbon.

II-2: Crystallite Size at Platinum (220) Plane

The XRD of the electrode catalyst in each of Examples and Comparative Examples was measured by an XRD apparatus (Rint2500; manufactured by Rigaku Corporation). The measurement conditions were as follows: Cu tube, 50 kV, and 300 mA. The crystallite size at a platinum (220) plane was determined according to the Scherrer equation on the basis of the obtained XRD spectrum.

II-3: Pore Size Distribution of Electrode Catalyst

Figure 2:
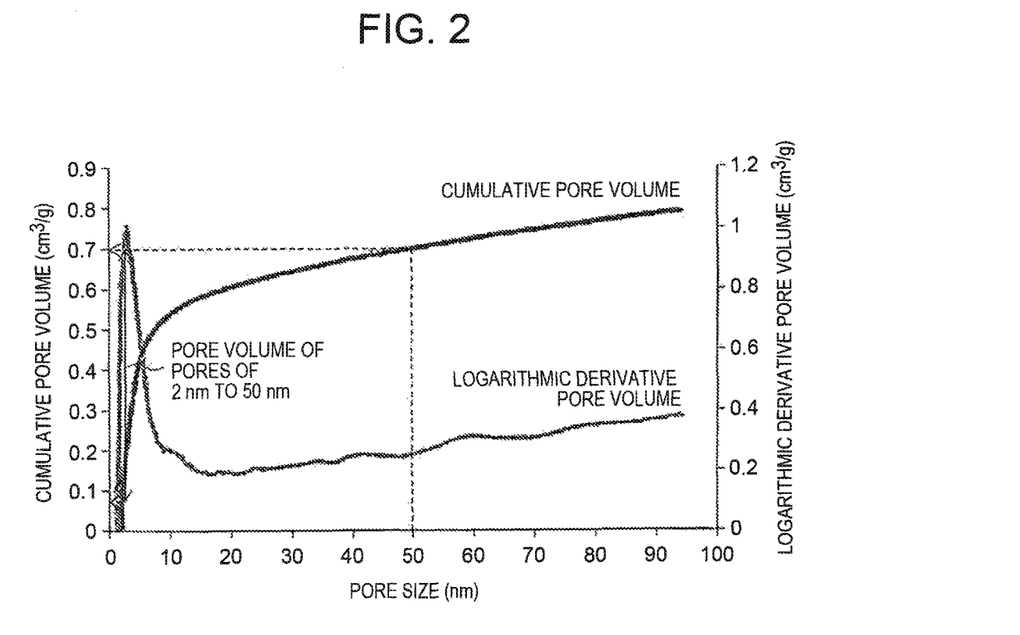
FIG. 2 is a diagram illustrating the pore size distribution of an electrode catalyst in Comparative Example 2, where the abscissa axis represents the pore size (nm) of the electrode catalyst, the left ordinate axis represents the cumulative pore volume ($cm^3/g$) of the electrode catalyst, and the right ordinate axis represents the logarithmic derivative pore volume ($cm^3/g$) of the electrode catalyst.
Figure 3:
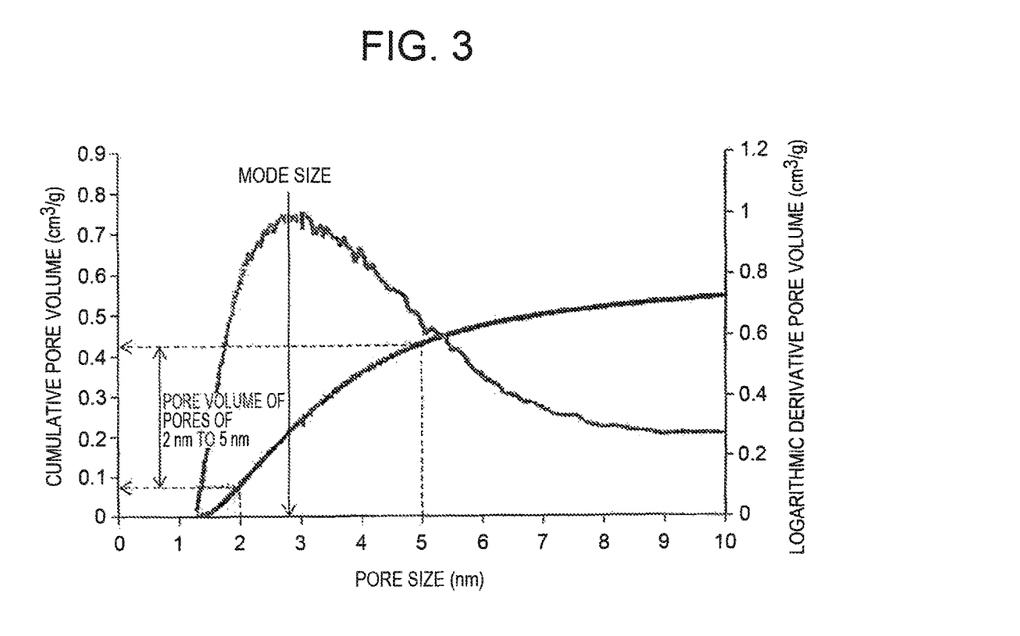
FIG. 3 is a diagram illustrating an enlarged view of a pore size range from 0 nm to 10 nm in the pore size distribution of the electrode catalyst in Comparative Example 2, where the abscissa axis represents the pore size (nm) of the electrode catalyst, the left ordinate axis represents the cumulative pore volume ($cm^3/g$) of the electrode catalyst, and the right ordinate axis represents the logarithmic derivative pore volume ($cm^3/g$) of the electrode catalyst.

A nitrogen gas adsorption isotherm of the electrode catalyst in each of Examples and Comparative Examples was determined by the constant volume method with the use of a pore size distribution measurement apparatus (3Flex; manufactured by Micromeritics Instrument Corporation). The pore size distribution was analyzed by the BJH method. The pore size distribution of the electrode catalyst in Comparative Example 2 is illustrated in FIG. 2 and FIG. 3. In FIG. 2 and FIG. 3, the abscissa axis represents the pore size (nm) of the electrode catalyst, the left ordinate axis represents the cumulative pore volume ($cm^3/g$) of the electrode catalyst, and the right ordinate axis represents the logarithmic derivative pore volume ($cm^3/g$) of the electrode catalyst.

As illustrated in FIG. 3, the mode size, which is a pore size that appeared most frequently in the electrode catalyst in Comparative Example 2, was approximately 2.7 nm. The pore volume of pores having pore sizes within the range from 2 nm to 5 nm was approximately 0.3 $cm^3/g$, and the pore volume of pores having pore sizes within the range from 2 nm to 50 nm was approximately 0.6 $cm^3/g$.

III: Production of MEA

III-1: Preparation of Electrode Catalyst Ink

One gram of the electrode catalyst was mixed with 10 mL of water, 5 mL of ethanol, and an ionomer (Nafion® DE2020; manufactured by E. I. du Pont de Nemours and Company) solution. The ionomer solution was used in such an amount that a ratio (I/C) of a mass (I) of solid matter in the ionomer with respect to a mass (C) of the carbon support included in the electrode catalyst was 0.75. The mixture was thoroughly stirred to be dispersed using a magnetic stirrer. The obtained dispersion was subjected to a dispersion treatment for 30 minutes using an ultrasonic homogenizer to prepare electrode catalyst ink.

III-2: Production of Electrode Catalyst Layer

A surface of a base material sheet was uniformly coated with the electrode catalyst ink obtained by the procedures of III-1. The base material sheet thus coated was dried at 80° C. for 3 hours to produce an electrode catalyst layer. The electrode catalyst ink was used in the coating such that the mass of Pt contained in the electrode catalyst per unit area on the coated surface was 0.2 mg/cm$^2$. A polytetrafluoroethylene (PTFE) sheet was used as the base material sheet.

IV-2: Gas Diffusion Resistance

The IV characteristics of the MEA in each of Examples and Comparative Examples were determined at 60° C. under low humidified (30% RH) or highly humidified (80% RH) conditions with reactive gas adjusted to a low oxygen concentration environment (hydrogen concentration: 100%, oxygen concentration: several %). A critical current density was calculated by dividing a value of current (critical current) of a portion at which the current value was not increased even if the voltage value was decreased in the IV characteristics by the surface area of the electrode catalyst layer. The gas diffusion resistance was determined by calculating the time required for one oxygen molecule to move 1 m, on the basis of the obtained critical current density, and the temperature, the relative humidity, and the oxygen concentration at the time of measurement.

V: Results of Evaluation of Electrode Catalyst and MEA

Table 2 illustrates the physical property values of the electrode catalysts of Examples and Comparative Examples and the performance values of the MEAs prepared using the electrode catalysts.

TABLE 2

| | Electrode catalyst | | | | Catalyst particle | | | MEA | | |
|---|---|---|---|---|---|---|---|---|---|---|
| | Pore volume (cm$^3$/g) | | | | Density of supported Pt (% by mass) | Density of supported Co (% by mass) | Pt (220) crystallite size (nm) | Mass activity (normalized) | Gas diffusion resistance (normalized) | |
| | Mode size (nm) | A: 2 nm to 5 nm | B: 2 nm to 50 nm | A/B | | | | | Low humidified | Highly humidified |
| Example 1 | 3.5 | 0.57 | 0.92 | 0.62 | 29.5 | 1.5 | 3.1 | 1.0 | 0.9 | 0.8 |
| Example 2 | 4.1 | 0.52 | 0.86 | 0.61 | 29.5 | 1.4 | 3.2 | 1.0 | 0.9 | 0.9 |
| Comparative Example 1 | 2.0 | 0.25 | 0.42 | 0.59 | 29.6 | 1.6 | 2.0 | 1.0 | 1.2 | 1.2 |
| Comparative Example 2 | 2.7 | 0.29 | 0.56 | 0.52 | 29.4 | 1.4 | 2.7 | 1 (reference) | 1 (reference) | 1 (reference) |

III-3: Production of MEA

Nafion® NR-211 (manufactured by E. I. du Pont de Nemours and Company) was used as a solid polymer electrolyte membrane. The electrode catalyst layer obtained by the procedures of III-2 was used in each of an anode and a cathode. The solid polymer electrolyte membrane was sandwiched between the anode and the cathode and joined together by hot pressing at 140° C. to produce an MEA.

IV: Evaluation of MEA

IV-1: Mass Activity

The dew point of each of the electrodes of the MEA in each of Examples and Comparative Examples was adjusted to 55° C., the relative humidity thereof was adjusted to 80%, and the temperature thereof was adjusted to 60° C. In this state, hydrogen (0.5 L/min, 50 kPa-G) was supplied to the anode while air (2 L/min, 50 kPa-G) was supplied to the cathode. A voltage value of 0.2 V at which surfaces of the electrode catalyst particles were temporarily in a reduced state was kept for several hours. Subsequently, the voltage value was increased from 0.1 V to 0.9 V by 0.1 V so as to be 0.1 V, 0.2 V, 0.3 V . . . . Each voltage value was kept for 3 minutes. The mass activity of the MEA in each of Examples and Comparative Examples was calculated by dividing a current density (A/cm$^2$) at 0.88 V by the total mass of Pt present on the surface of the electrode on the cathode side.

As illustrated in Table 2, the MEAs produced using the electrode catalysts in Examples 1, 2 had a mass activity substantially equal to that of the MEAs produced using the electrode catalysts in Comparative Examples 1, 2, and exhibited gas diffusion resistance lower by approximately 20% than that of the MEAs produced using the electrode catalysts in Comparative Examples 1, 2.

What is claimed is:

1. A fuel cell electrode catalyst comprising:
   a carbon support having pores having a mode pore size within a range from 2 nm to 5 nm, wherein, in the pores of the fuel cell electrode catalyst, a pore volume of pores having pore sizes within the range from 2 nm to 5 nm is 0.4 cm$^3$/g or larger, and a ratio of the pore volume of the pores having pore sizes within the range from 2 nm to 5 nm with respect to a pore volume of pores having pore sizes within a range from 2 nm to 50 nm is 0.55 or higher; and
   catalyst particles supported on the carbon support, containing platinum or a platinum alloy, and having a crystallite size within the range from 2 nm to 5 nm at a platinum (220) plane, wherein
   a density of the supported catalyst particles is within a range from 10% by mass to 50% by mass with respect to a total mass of the fuel cell electrode catalyst.

2. A fuel cell comprising the fuel cell electrode catalyst according to claim 1.

3. A method of producing the fuel cell electrode catalyst according to claim 1, the method comprising:
- preparing a metal-containing solution containing a metal or a salt of the metal;
- forming metal acetylide by mixing the metal-containing solution with acetylene gas;
- subjecting the metal acetylide to a first heat treatment at a temperature within a range from 40° C. to 80° C. to form a metal particle-containing intermediate;
- subjecting the metal particle-containing intermediate to a second heat treatment while a temperature is increased to a value within a range from 100° C. to 200° C. at a rate of temperature increase that is within a range from 5° C./min to 50° C./min, to cause the metal, which is contained in the metal particle-containing intermediate, to spout from the metal particle-containing intermediate to obtain a carbon support having pores;
- causing the carbon support obtained through the second heat treatment to react with a catalytic metal material containing a salt of a catalytic metal, to cause the catalytic metal material to be supported on the carbon support; and
- forming platinum or a platinum alloy in a metal form by reducing the salt of the catalytic metal contained in the catalytic metal material supported on the carbon support.

* * * * *